United States Patent
Clough et al.

[11] Patent Number: 5,942,509
[45] Date of Patent: Aug. 24, 1999

[54] FUNGICIDES

[75] Inventors: John Martin Clough, Marlow; Christopher Richard Ayles Godfrey, Bracknell; Paul John De Fraine; Ian Thomas Streeting, both of Wokingham; Gordon Richard Munns, Reading, all of United Kingdom

[73] Assignee: Zeneca Limited, United Kingdom

[21] Appl. No.: 08/791,930

[22] Filed: Jan. 31, 1997

Related U.S. Application Data

[63] Continuation of application No. 08/118,410, Sep. 8, 1993, abandoned, which is a continuation of application No. 07/779,413, Oct. 15, 1991, abandoned.

[30] Foreign Application Priority Data

Oct. 25, 1990 [GB] United Kingdom ............... 9023294

[51] Int. Cl.⁶ ............. A61K 31/53; C07D 251/26; C07D 251/38; C07D 253/07
[52] U.S. Cl. ............. 514/241; 514/242; 514/245; 544/182; 544/194; 544/208; 544/211; 544/213; 544/218; 544/219
[58] Field of Search ............. 514/241, 242, 514/245; 544/182, 194, 204, 208, 211, 213, 218, 219

[56] References Cited

U.S. PATENT DOCUMENTS 4,931,438  6/1990  Clough et al. ............ 514/241
5,057,146  10/1991  Anthony et al. ............ 71/94
5,124,329  6/1992  Clough et al. ............ 514/241

FOREIGN PATENT DOCUMENTS 307103  3/1989  European Pat. Off.

OTHER PUBLICATIONS

Elliot et al, Chem. Soc. Rev. vol. 7, pp. 473–505, 1978.

*Primary Examiner*—Yogendra N. Gupta
*Attorney, Agent, or Firm*—Marian T. Thomson

[57] ABSTRACT

Fungicidal compounds having the formula (I):

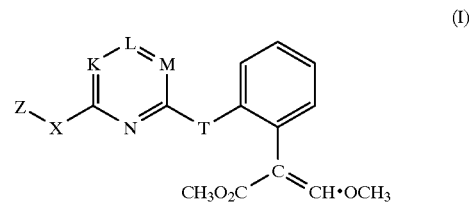

(I)

in which any two of K, L and M are nitrogen and the other is CA wherein A is H, halogen, $C_{1-4}$ alkyl, cyano, nitro or trifluoromethyl; X is a linking group other than oxygen; T is oxygen or sulphur; and Z is an optionally substituted carbocyclic or heterocyclic ring.

8 Claims, No Drawings

FUNGICIDES

This application is a continuation of copending application Ser. No. 08/118,410, filed Sep. 8, 1993, which in turn is a continuation of Ser. No. 07/779,413, filed Oct. 15, 1991, now abandoned.

This invention relates to derivatives of propenoic acid useful as fungicides, to processes for preparing them, to fungicidal compositions containing them, and to methods of using them to combat fungi, especially fungal infections of plants.

There is described in EP-A-0260794 a range of fungicidal compounds which are methyl 2-(optionally substituted)heterocyclyloxy(or thio)phenyl-3-methoxypropenoates. The heterocyclic ring is six-membered, C-linked and contains 2 to 4 nitrogen atoms. Included are triazinyloxy compounds.

According to the present invention there are provided compounds having the formula (I), in which any two of K, L and M are nitrogen and the other is CA wherein A is H, halogen, $C_{1-4}$ alkyl (for example, methyl), $C_{1-4}$ alkoxy (for example, methoxy), cyano, nitro or trifluoromethyl; X is a linking group other than oxygen; T is oxygen or sulphur; and Z is an optionally substituted carbocyclic or heterocyclic ring.

Because of the unsymmetrically substituted double bond of the propenoate group, the compounds of the invention may be obtained in the form of mixtures of (E)- and (Z)-geometric isomers. However, these mixtures can be separated into individual isomers, and this invention embraces such isomers and mixtures thereof in all proportions including those which consist substantially of the (Z)-isomer and those which consist substantially of the (E)-isomer. The (E)-isomer, in which the groups —$CO_2CH_3$ and —$OCH_3$ are on opposite sides of the olefinic bond of the propenoate group, are the more fungicidally active and form a preferred embodiment of the invention.

The ring containing K, L and M in formula (I) is a triazine ring. It may be a symmetrical triazine ring in which K and M are both nitrogen and L is CA or an unsymmetrical triazine ring in which either K and L are both nitrogen and M is CA or L and M are both nitrogen and K is CA.

The group A is typically H or halogen, suitably chlorine.

The group X may be, for example, $S(O)_n$, $NR^4$, $N(CHO)$, $CR^1R^2$, $CHR^6$, CO, $CR^1$ ($OR^2$), C=$CR^1R^2$, $CHR^1CHR^2$, $CR^1$=$CR^2$, $CHR^1CR^2$=CH, C≡C, $OCHR^1$, $CHR^1O$, $CH(CF_3)O$, $CH(CN)O$, $OCHR^1O$, $S(O)_nCHR^1$, $S(O)_nCHR^1O$, $CHR^1S(O)_n$, $CHR^1OSO_2$, $NR^4CHR^1$, $CHR^1NR^4$, $CO_2$, $O_2C$, $SO_2O$, $OSO_2$, CO.CO, $COCHR^1$, $COCHR^1O$, $CHR^1CO$, CHOH.$CHR^1$, $CHR^1$.CHOH, Ψ, Ω (for the meaning of Ψ and Ω see under "Chemical Formulae" later), $CONR^4$, $OCONR^4$, $NR^4CO$, $CSNR^4$, $OCS.NR^4$, $SCO.NR^4$, $NR^4CO_2$, $NR^4CS$, $NR^4CSO$, $NR^4COS$, $NR^4CONR$, $S(O)_nNR^4$, $NR^4S(O)_n$, $Cs_2$, $S_2C$, CO.S, SCO, N=N, N=$CR^1$, $CR^1$=N, $CHR^1CHR^2CH(OH)$, $CHR^1OCO$, $CHR^1SCO$, $CHR^1NR^4CO$, $CHR^1NR^4CONR^4$, $CHR^1CHR^2CO$, O.N=$CR^1$, $CHR^1O.N$=$CR^2$, $CO.OCR^1R^2$, $CHR^1CHR^2CHR^3$, $OCHR^1CHR^2$, $(CH_2)_mO$, $CHR^1OCHR^2$, $CHR^1CHR^2O$, $OCHR^1CHR^2O$, $S(O)_nCHR^1CHR^2$, $SCHR^1CHR^2$, $CHR^1S(O)_nCHR^2$, $CHR^1CHR^2S(O)_n$, $CR^1$=$NNR^4$, $CR^1$=NO, $NR^4N$=$CR^1$, $CHR^1CONR^2$, $CHR^1OCO.NR^2$, CH=$CHCH_2O$, C≡$CCH_2O$, $COCHR^1CHR^2O$, or $(R^5)_2P^+CHR^2Q^-$; where $R^1$, $R^2$ and $R^3$, which may be the same or different, are H, $C_{1-4}$ alkyl or phenyl; $R^4$ is H, $C_{1-4}$ alkyl or $COR^1$; $R^5$ is optionally substituted phenyl; $R^6$ is substituted phenyl; $Q^-$ is a halide anion; n is 0, 1 or 2; and m is 3, 4 or 5.

The substituent Z in compound (I) is optionally substituted carbocyclyl or optionally substituted heterocyclyl, this group being linked in each case to the group X through any of its atoms which valency allows. Where valency allows, each of the optionally substituted carbocyclyl or heterocyclyl groups can carry up to 5 substitutents.

The term "carbocyclyl" includes aromatic and non-aromatic rings such as, for example, phenyl, naphthyl, cyclopentyl, cyclohexyl and cyclohexenyl, the preferred value being phenyl.

The term "heterocyclyl" includes 5- and 6-membered aromatic and non-aromatic heterocyclic rings containing one or more of each of the heteroatoms O, S and N (preferably S or N), fused benzenoid and heteroaromatic ring systems, and, in each case, the corresponding N-oxides; heteroaromatic ring systems are preferred. Examples of heterocyclyl groups which Z may be are pyridinyl, pyrimidinyl, pyrazinyl, pyridazinyl, 1,2,3-, 1,2,4-, and 1,3,5-triazinyl, 1,2,4,5-tetrazinyl, 1,2,3- and 1,2,4-triazolyl, thienyl, furyl, pyrrolyl, thiazolyl, purinyl, oxadiazolyl, quinolinyl, isoquinolinyl, quinoxalinyl, benzothienyl, benzoxazolyl, benzthiazolyl, tetrahydrofuryl, morpholinyl and piperidinyl and, where appropriate, the corresponding N-oxides.

Substituents which may be present in the optionally substituted carbocyclyl and heterocyclyl moieties include one or more of the following: halo, hydroxy, oxo, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$alkoxy($C_{1-4}$)-alkyl, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridinyl or pyrimidinyl), optionally substituted aryloxy (especially optionally substituted phenoxy), optionally substituted heteroaryloxy (especially optionally substituted pyridinyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridinyl- or pyrimidinyl($C_{1-4}$)alkyl), optionally substituted aryl($C_{2-4}$)alkenyl (especially optionally substituted phenylethenyl), optionally substituted heteroaryl($C_{2-4}$) alkenyl (especially optionally substituted pyridinylethenyl or pyrimidinylethenyl), optionally substituted aryl($C_{1-4}$)alkoxy (especially optionally substitued benzyloxy), optionally substituted heteroaryl($C_{1-4}$)-alkoxy (especially optionally substituted pyridinyl- or pyrimidinyl($C_{1-4}$)-alkoxy), optionally substituted aryloxy($C_{1-4}$)alkyl (especially phenoxy-methyl), optionally substituted heteroaryloxy($C_{1-4}$)alkyl (especially optionally substituted pyridinyloxy- or pyrimidinyloxy($C_{1-4}$)alkyl), acyloxy, including $C_{1-4}$ alkanoyloxy (especially acetyloxy) and benzoyloxy, cyano, thiocyanato, nitro, —NR'R", —NHCOR', —NHCONR'R", —CONR'R", —COOR', —$OSO_2R'$, —$SO_2R'$, —COR', —CR'=NR"or—N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl ($C_{1-4}$)alkyl, phenyl or benzyl, the phenyl and benzyl groups being optionally substituted with halogen, $C_{1-4}$ alkyl or $C_{1-4}$ alkoxy. Or substituents, when ortho to one another, join to form a 5- or 6-membered ring.

Substituents which may be present in the aryl or heteroaryl rings of any of the foregoing substituents and in the phenyl ring of $R^5$ and $R^6$ include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$ )alkyl, halo($C_{1-4}$ )alkoxy, $C_{1-4}$ alkylthio, hydroxy ($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —OSO$_2$R', —SO$_2$R', —COR', —CR'═NR" or —N═CR'R" in which R' and R" have the meanings given above.

In one aspect the invention includes compounds having the formula (I) in which K and M are both nitrogen; L is CH; Z is optionally substituted phenyl and X is as defined above. Suitably X is S, CH$_2$O, CH$_2$S, CH$_2$CH$_2$O or CH$_2$CH$_2$CH$_2$O.

In a particular aspect the invention includes a compound having the formula (I.1) in which Z is phenyl optionally substituted with halo, $C_{1-4}$ alkyl or trifluoromethyl; and X is S, CH$_2$O, CH$_2$S, CH$_2$CH$_2$O, CH$_2$CH$_2$CH$_2$O or (E) —CH═NO.

In another particular aspect the invention includes a compound having the formula (I.2) in which Z is phenyl optionally substituted with $C_{1-4}$ alkyl; X is S; and A is H or Cl.

The invention is illustrated by the compounds listed in Tables I to VI which follow. The compounds of Tables I to VI have the formulae (I.3) to (I.8), respectively, in which the values of Z and X are given in Tables I and III to VI and the values of Z, X and A are given in Table II. Throughout the Tables the methyl 3-methoxypropenoate group has the (E)-configuration.

TABLE I (Formula (I.3))

| Compound No | Z | X |
|---|---|---|
| 1 | C$_6$H$_5$ | S |
| 2 | C$_6$H$_5$ | SO |
| 3 | C$_6$H$_5$ | SO$_2$ |
| 4 | C$_6$H$_5$ | NH |
| 5 | C$_6$H$_5$ | NCH$_3$ |
| 6 | C$_6$H$_5$ | NCH$_2$CH$_3$ |
| 7 | C$_6$H$_5$ | NCOCH$_3$ |
| 8 | C$_6$H$_5$ | NCH(CH$_3$)$_2$ |
| 9 | C$_6$H$_5$ | CH$_2$ |
| 10 | C$_6$H$_5$ | CH(CH$_3$) |
| 11 | C$_6$H$_5$ | C(CH$_3$)$_2$ |
| 12 | C$_6$H$_5$ | CO |
| 13 | C$_6$H$_5$ | C═CH$_2$ |
| 14 | C$_6$H$_5$ | C═C(CH$_3$)$_2$ |
| 15 | C$_6$H$_5$ | CH$_2$CH$_2$ |
| 16 | C$_6$H$_5$ | CH(CH$_3$)CH$_2$ |
| 17 | C$_6$H$_5$ | CH$_2$CH(CH$_3$) |
| 18 | C$_6$H$_5$ | (E)-CH═CH |
| 19 | C$_6$H$_5$ | (E)-C(CH$_3$)═C(CH$_3$) |
| 20 | C$_6$H$_5$ | C≡C |
| 21 | C$_6$H$_5$ | OCH$_2$ |
| 22 | C$_6$H$_5$ | OCH(CH$_3$) |
| 23 | C$_6$H$_5$ | CH$_2$O |
| 24 | C$_6$H$_5$ | CH(CH$_3$)O |
| 25 | C$_6$H$_5$ | SCH$_2$ |
| 26 | C$_6$H$_5$ | SCH(CH$_3$) |
| 27 | C$_6$H$_5$ | S(O)CH$_2$ |
| 28 | C$_6$H$_5$ | S(O)CH(CH$_3$) |
| 29 | C$_6$H$_5$ | S(O)$_2$CH$_2$ |
| 30 | C$_6$H$_5$ | S(O)$_2$CH(CH$_3$) |
| 31 | C$_6$H$_5$ | CH$_2$S |
| 32 | C$_6$H$_5$ | CH(CH$_3$)S |
| 33 | C$_6$H$_5$ | CH$_2$S(O) |
| 34 | C$_6$H$_5$ | CH(CH$_3$)S(O) |

TABLE I-continued (Formula (I.3))

| Compound No | Z | X |
|---|---|---|
| 35 | C$_6$H$_5$ | CH$_2$S(O)$_2$ |
| 36 | C$_6$H$_5$ | CH(CH$_3$)S(O)$_2$ |
| 37 | C$_6$H$_5$ | NHCH$_2$ |
| 38 | C$_6$H$_5$ | N(CH$_3$)CH$_2$ |
| 39 | C$_6$H$_5$ | N(COCH$_3$)CH$_2$ |
| 40 | C$_6$H$_5$ | NHCH(CH$_3$) |
| 41 | C$_6$H$_5$ | N(CH$_3$)CH(CH$_3$) |
| 42 | C$_6$H$_5$ | N(COCH$_3$)CH(CH$_3$) |
| 43 | C$_6$H$_5$ | CH$_2$NH |
| 44 | C$_6$H$_5$ | CH$_2$N(CH$_3$) |
| 45 | C$_6$H$_5$ | CH$_2$N(COCH$_3$) |
| 46 | C$_6$H$_5$ | CH(CH$_3$)NH |
| 47 | C$_6$H$_5$ | CH(CH$_3$)N(CH$_3$) |
| 48 | C$_6$H$_5$ | CH(CH$_3$)N(COCH$_3$) |
| 49 | C$_6$H$_5$ | CO$_2$ |
| 50 | C$_6$H$_5$ | O$_2$C |
| 51 | C$_6$H$_5$ | SO$_2$O |
| 52 | C$_6$H$_5$ | OSO$_2$ |
| 53 | C$_6$H$_5$ | CO.CO |
| 54 | C$_6$H$_5$ | COCH$_2$ |
| 55 | C$_6$H$_5$ | COCH(CH$_3$) |
| 56 | C$_6$H$_5$ | CH$_2$CO |
| 57 | C$_6$H$_5$ | CH(CH$_3$)CO |
| 58 | C$_6$H$_5$ | CH(OH)CH$_2$ |
| 59 | C$_6$H$_5$ | CH(OH)CH(CH$_3$) |
| 60 | C$_6$H$_5$ | CH$_2$CH(OH) |
| 61 | C$_6$H$_5$ | CH(CH$_3$)CH(OH) |
| 62 | C$_6$H$_5$ | CONH |
| 63 | C$_6$H$_5$ | CON(CH$_3$) |
| 64 | C$_6$H$_5$ | CON(CH$_2$CH$_2$CH$_3$) |
| 65 | C$_6$H$_5$ | CON(CHO) |
| 66 | C$_6$H$_5$ | CON(COCH$_3$) |
| 67 | C$_6$H$_5$ | NHCO |
| 68 | C$_6$H$_5$ | N(CH$_3$)CO |
| 69 | C$_6$H$_5$ | N(CH$_2$CH$_3$)CO |
| 70 | C$_6$H$_5$ | N(CHO)CO |
| 71 | C$_6$H$_5$ | N(COCH$_3$)CO |
| 72 | C$_6$H$_5$ | CSN(CH$_3$) |
| 73 | C$_6$H$_5$ | CSNH |
| 74 | C$_6$H$_5$ | NHCS |
| 75 | C$_6$H$_5$ | N(CH$_3$)CS |
| 76 | C$_6$H$_5$ | SO$_2$NH |
| 77 | C$_6$H$_5$ | SO$_2$N(CH$_3$) |
| 78 | C$_6$H$_5$ | NHSO$_2$ |
| 79 | C$_6$H$_5$ | N(CH$_3$)SO$_2$ |
| 80 | C$_6$H$_5$ | N(CH$_2$CH$_3$)SO$_2$ |
| 81 | C$_6$H$_5$ | CS$_2$ |
| 82 | C$_6$H$_5$ | S$_2$C |
| 83 | C$_6$H$_5$ | COS |
| 84 | C$_6$H$_5$ | SCO |
| 85 | C$_6$H$_5$ | (E)-N═N |
| 86 | C$_6$H$_5$ | (E)-N═CH |
| 87 | C$_6$H$_5$ | (E)-N═C(CH$_3$) |
| 88 | C$_6$H$_5$ | (E)-CH═N |
| 89 | C$_6$H$_5$ | (E)-C(CH$_3$)═N |
| 90 | C$_6$H$_5$ | CH$_2$CH$_2$CH$_2$ |
| 91 | C$_6$H$_5$ | CH(CH$_3$)CH$_2$CH$_2$ |
| 92 | C$_6$H$_5$ | CH$_2$CH(CH$_3$)CH$_2$ |
| 93 | C$_6$H$_5$ | CH$_2$CH$_2$CH(CH$_3$) |
| 94 | C$_6$H$_5$ | OCH$_2$CH$_2$ |
| 95 | C$_6$H$_5$ | CH$_2$OCH$_2$ |
| 96 | C$_6$H$_5$ | CH$_2$CH$_2$O |
| 97 | C$_6$H$_5$ | SCH$_2$CH$_2$ |
| 98 | C$_6$H$_5$ | S(O)CH$_2$CH$_2$ |
| 99 | C$_6$H$_5$ | S(O)$_2$CH$_2$CH$_2$ |
| 100 | C$_6$H$_5$ | CH$_2$SCH$_2$ |
| 101 | C$_6$H$_5$ | CH$_2$S(O)CH$_2$ |
| 102 | C$_6$H$_5$ | CH$_2$S(O)$_2$CH$_2$ |
| 103 | C$_6$H$_5$ | CH$_2$CH$_2$S |
| 104 | C$_6$H$_5$ | CH$_2$CH$_2$S(O) |
| 105 | C$_6$H$_5$ | CH$_2$CH$_2$S(O)$_2$ |
| 106 | C$_6$H$_5$ | (E)-CH═NNH |
| 107 | C$_6$H$_5$ | (E)-C(CH$_3$)═NNH |
| 108 | C$_6$H$_5$ | (E)-CH═NN(CH$_3$) |

TABLE I-continued (Formula (I.3))

| Compound No | Z | X |
|---|---|---|
| 109 | $C_6H_5$ | (E)-NHN = CH |
| 110 | $C_6H_5$ | (E)-NHN = C(CH$_3$) |
| 111 | $C_6H_5$ | (E)-N(CH$_3$)N = CH |
| 112 | $C_6H_5$ | CH$_2$CONH |
| 113 | $C_6H_5$ | CH(CH$_3$)CON(CH$_3$) |
| 114 | $C_6H_5$ | CH(CH$_3$)CON(CH$_3$) |
| 115 | $C_6H_5$ | (E)-CH = CHCH$_2$O |
| 116 | $C_6H_5$ | COCH$_2$CH$_2$O |
| 117 | $C_6H_5$ | * |
| 118 | $C_6H_5$ | * |
| 119 | 2-Cl—C$_6$H$_4$ | S |
| 120 | 3-Cl—C$_6$H$_4$ | N(CH$_3$) |
| 121 | 4-Cl—C$_6$H$_4$ | NH |
| 122 | 2-F—C$_6$H$_4$ | OCH$_2$ |
| 123 | 3-F—C$_6$H$_4$ | CH$_2$O |
| 124 | 4-F—C$_6$H$_4$ | S |
| 125 | 2-CH$_3$—C$_6$H$_4$ | N(CH$_3$) |
| 126 | 3-CH$_3$—C$_6$H$_4$ | CH$_2$ |
| 127 | 4-CH$_3$—C$_6$H$_4$ | OCH$_2$ |
| 128 | 2-CH$_3$O—C$_6$H$_4$ | CH$_2$O |
| 129 | 3-CH$_3$O—C$_6$H$_4$ | S |
| 130 | 4-CH$_3$O—C$_6$H$_4$ | N(CH$_3$) |
| 131 | 2-NO$_2$—C$_6$H$_4$ | NH |
| 132 | 3-NO$_2$—C$_6$H$_4$ | OCH$_2$ |
| 133 | 4-F—C$_6$H$_4$ | CH$_2$O |
| 134 | 2-Cyano-C$_6$H$_4$ | S |
| 135 | 3-Cyano-C$_6$H$_4$ | N(CH$_3$) |
| 136 | 4-Cyano-C$_6$H$_4$ | CH$_2$ |
| 137 | 2-Br—C$_6$H$_4$ | OCH$_2$ |
| 138 | 3-Br—C$_6$H$_4$ | CH$_2$O |
| 139 | 4-Br—C$_6$H$_4$ | S |
| 140 | 2-CF$_3$—C$_6$H$_4$ | N(CH$_3$) |
| 141 | 3-CF$_3$—C$_6$H$_4$ | NH |
| 142 | 4-CF$_3$—C$_6$H$_4$ | OCH$_2$ |
| 143 | 2-C$_6$H$_5$O—C$_6$H$_4$ | CH$_2$O |
| 144 | 3-C$_6$H$_5$O—C$_6$H$_4$ | S |
| 145 | 4-C$_6$H$_5$O—C$_6$H$_4$ | N(CH$_3$) |
| 146 | 2-CH$_3$CH$_2$O—C$_6$H$_4$ | CH$_2$ |
| 147 | 3-CH$_3$CH$_2$O—C$_6$H$_4$ | OCH$_2$ |
| 148 | 4-CH$_3$CH$_2$O—C$_6$H$_4$ | CH$_2$O |
| 149 | 2-C$_6$H$_5$—C$_6$H$_4$ | S |
| 150 | 3-C$_6$H$_5$—C$_6$H$_4$ | N(CH$_3$) |
| 151 | 4-C$_6$H$_5$—C$_6$H$_4$ | NH |
| 152 | 2,3-di-Cl—C$_6$H$_3$ | OCH$_2$ |
| 153 | 2,4-di-Cl—C$_6$H$_3$ | CH$_2$O |
| 154 | 2,5-di-Cl—C$_6$H$_3$ | S |
| 155 | 2,6-di-Cl—C$_6$H$_3$ | N(CH$_3$) |
| 156 | 3,4-di-Cl—C$_6$H$_3$ | CH$_2$ |
| 157 | 3,5-di-Cl—C$_6$H$_3$ | OCH$_2$ |
| 158 | 2-Cl-3-CH$_3$O—C$_6$H$_3$ | CH$_2$O |
| 159 | 2-Cl-4-CH$_3$O—C$_6$H$_3$ | S |
| 160 | 2-Cl-5-CH$_3$O—C$_6$H$_3$ | N(CH$_3$) |
| 161 | 2-Cl-6-CH$_3$O—C$_6$H$_3$ | NH |
| 162 | 3-Cl-4-CH$_3$O—C$_6$H$_3$ | OCH$_2$ |
| 163 | 3-Cl-5-CH$_3$O—C$_6$H$_3$ | CH$_2$O |
| 164 | 2-CH$_3$O-3-Cl—C$_6$H$_3$ | S |
| 165 | 2-CH$_3$O-4-Cl—C$_6$H$_3$ | N(CH$_3$) |
| 166 | 2-CH$_3$O-5-Cl—C$_6$H$_3$ | CH$_2$ |
| 167 | 3-CH$_3$O-4-Cl—C$_6$H$_3$ | OCH$_2$ |
| 168 | 1-Naphthyl | CH$_2$O |
| 169 | 2-Naphthyl | S |
| 170 | 2-(E)-(CH$_3$O$_2$C.C = CH.OCH$_3$)C$_6$H$_4$ | N(CH$_3$) |
| 171 | 2-(E)-(CH$_3$O$_2$C.C = CH.OCH$_3$)C$_6$H$_4$ | NH |
| 172 | 2-(E)-(CH$_3$O$_2$C.C = CH.OCH$_3$)C$_6$H$_4$ | OCH$_2$ |
| 173 | 2-(E)-(CH$_3$O$_2$C.C = CH.OCH$_3$)C$_6$H$_4$ | CH$_2$O |
| 174 | 2-(E)-(CH$_3$O$_2$C.C = CH.OCH$_3$)C$_6$H$_4$ | S |
| 175 | C$_6$F$_5$ | N(CH$_3$) |
| 176 | 2,6-di-F—C$_6$H$_3$ | CH$_2$ |
| 177 | 2-Cyano-6-F—C$_6$H$_3$ | OCH$_2$ |
| 178 | 3-Cyano-4,6-di-F—C$_6$H$_2$ | CH$_2$O |
| 179 | 2,6-di-Cyano-C$_6$H$_3$ | S |
| 180 | Pyridin-2-yl | S |
| 181 | Pyridin-2-yl | N(CH$_3$) |
| 182 | Pyridin-2-yl | NH |
| 183 | Pyridin-2-yl | OCH$_2$ |
| 184 | Pyridin-2-yl | CH$_2$O |
| 185 | Pyridin-2-yl | CH$_2$CH$_2$O |
| 186 | Pyridin-2-yl | CH$_2$CH$_2$CH$_2$O |
| 187 | Pyridin-3-yl | S |
| 188 | Pyridin-3-yl | N(CH$_3$) |
| 189 | Pyridin-3-yl | NH |
| 190 | Pyridin-3-yl | OCH$_2$ |
| 191 | Pyridin-3-yl | CH$_2$O |
| 192 | Pyridin-3-yl | CH$_2$CH$_2$O |
| 193 | Pyridin-3-yl | CH$_2$CH$_2$CH$_2$O |
| 194 | Pyridin-4-yl | S |
| 195 | Pyridin-4-yl | N(CH$_3$) |
| 196 | Pyridin-4-yl | NH |
| 197 | Pyridin-4-yl | OCH$_2$ |
| 198 | Pyridin-4-yl | CH$_2$O |
| 199 | Pyridin-4-yl | CH$_2$CH$_2$O |
| 200 | Pyridin-4-yl | CH$_2$CH$_2$CH$_2$O |
| 201 | Pyrimidin-2-yl | S |
| 202 | Pyrimidin-2-yl | N(CH$_3$) |
| 203 | Pyrimidin-2-yl | NH |
| 204 | Pyrimidin-2-yl | OCH$_2$ |
| 205 | Pyrimidin-2-yl | CH$_2$O |
| 206 | Pyrimidin-2-yl | CH$_2$CH$_2$O |
| 207 | Pyrimidin-2-yl | CH$_2$CH$_2$CH$_2$O |
| 208 | Pyrimidin-4-yl | S |
| 209 | Pyrimidin-4-yl | N(CH$_3$) |
| 210 | Pyrimidin-4-yl | NH |
| 211 | Pyrimidin-4-yl | OCH$_2$ |
| 212 | Pyrimidin-4-yl | CH$_2$O |
| 213 | Pyrimidin-4-yl | CH$_2$CH$_2$O |
| 214 | Pyrimidin-4-yl | CH$_2$CH$_2$CH$_2$O |
| 215 | Pyrimidin-5-yl | S |
| 216 | Pyrimidin-5-yl | N(CH$_3$) |
| 217 | Pyrimidin-5-yl | NH |
| 218 | Pyrimidin-5-yl | OCH$_2$ |
| 219 | Pyrimidin-5-yl | CH$_2$O |
| 220 | Pyrimidin-5-yl | CH$_2$CH$_2$O |
| 221 | Pyrimidin-5-yl | CH$_2$CH$_2$CH$_2$O |
| 222 | Pyrazin-2-yl | S |
| 223 | Pyrazin-2-yl | N(CH$_3$) |
| 224 | Pyrazin-2-yl | NH |
| 225 | Pyrazin-2-yl | OCH$_2$ |
| 226 | Pyrazin-2-yl | CH$_2$O |
| 227 | Pyrazin-2-yl | CH$_2$CH$_2$O |
| 228 | Pyrazin-2-yl | CH$_2$CH$_2$CH$_2$O |
| 229 | Pyridazin-3-yl | S |
| 230 | Pyridazin-3-yl | N(CH$_3$) |
| 231 | Pyridazin-3-yl | NH |
| 232 | Pyridazin-3-yl | OCH$_2$ |
| 233 | Pyridazin-3-yl | CH$_2$O |
| 234 | Pyridazin-3-yl | CH$_2$CH$_2$O |
| 235 | Pyridazin-3-yl | CH$_2$CH$_2$CH$_2$O |
| 236 | Pyridazin-4-yl | S |
| 237 | Pyridazin-4-yl | N(CH$_3$) |
| 238 | Pyridazin-4-yl | NH |
| 239 | Pyridazin-4-yl | OCH$_2$ |
| 240 | Pyridazin-4-yl | CH$_2$O |
| 241 | Pyridazin-4-yl | CH$_2$CH$_2$O |
| 242 | Pyridazin-4-yl | CH$_2$CH$_2$CH$_2$O |
| 243 | 1,2,4-Triazin-3-yl | S |
| 244 | 1,2,4-Triazin-3-yl | N(CH$_3$) |
| 245 | 1,2,4-Triazin-5-yl | NH |
| 246 | 1,2,4-Triazin-5-yl | OCH$_2$ |
| 247 | 1,2,4-Triazin-6-yl | CH$_2$O |
| 248 | 1,2,4-Triazin-6-yl | CH$_2$CH$_2$O |
| 249 | 1,3,5-Triazin-2-yl | CH$_2$CH$_2$CHO |
| 250 | 1,3,5-Triazin-2-yl | S |
| 251 | 1,3,5-Triazin-2-yl | N(CH$_3$) |

TABLE I-continued

(Formula (I.3))

| Compound No | Z | X |
|---|---|---|
| 252 | Quinolin-2-yl | NH |
| 253 | Quinolin-2-yl | $OCH_2$ |
| 254 | Quinolin-2-yl | $CH_2O$ |
| 255 | Isoquinolin-1-yl | $CH_2CH_2O$ |
| 256 | Isoquinolin-1-yl | $CH_2CH_2CH_2O$ |
| 257 | Isoquinolin-1-yl | S |
| 258 | Benzoxazol-2-yl | $N(CH_3)$ |
| 259 | Benzoxazol-2-yl | NH |
| 260 | Benzoxazol-2-yl | $OCH_2$ |
| 261 | Benzthiazol-2-yl | $CH_2O$ |
| 262 | Benzthiazol-2-yl | $CH_2CH_2O$ |
| 263 | Benzthiazol-2-yl | $CH_2CH_2CH_2O$ |
| 264 | Thien-2-yl | S |
| 265 | Thien-2-yl | $N(CH_3)$ |
| 266 | Thien-2-yl | NH |
| 267 | Thien-3-yl | $OCH_2$ |
| 268 | Thien-3-yl | $CH_2O$ |
| 269 | Thien-3-yl | $CH_2CH_2O$ |
| 270 | 1,2,4-Triazol-1-yl | $CH_2CH_2CH_2O$ |
| 271 | Quinazolin-4-yl | S |
| 272 | Quinazolin-4-yl | $N(CH_3)$ |
| 273 | Quinolin-4-yl | NH |
| 274 | Quinolin-4-yl | $OCH_2$ |
| 275 | Purin-6-yl | $CH_2O$ |
| 276 | Thiazol-2-yl | $CH_2CH_2O$ |
| 277 | Thiazol-2-yl | $CH_2CH_2CH_2O$ |
| 278 | Thiazol-4-yl | S |
| 279 | Thiazol-4-yl | $N(CH_3)$ |
| 280 | Thiazol-5-yl | NH |
| 281 | Thiazol-5-yl | $OCH_2$ |
| 282 | Furan-2-yl | $CH_2O$ |
| 283 | N—$CH_3$-Pyrrol-2-yl | $CH_2CH_2O$ |
| 284 | N—$CH_3$-Pyrrol-2-yl | $CH_2CH_2CH_2O$ |
| 285 | 5-$CF_3$-Pyridin-2-yl | S |
| 286 | 3-F-Pyridin-2-yl | $N(CH_3)$ |
| 287 | 3-Cl-Pyridin-2-yl | NH |
| 288 | 4-Br-Pyridin-2-yl | $OCH_2$ |
| 289 | 3-$CH_3$-Pyridin-2-yl | $CH_2O$ |
| 290 | 6-$CH_3O$-Pyridin-2-yl | $CH_2CH_2O$ |
| 291 | 4,6-di-F-Pyridin-2-yl | $CH_2CH_2CH_2O$ |
| 292 | 2-Cl-Pyridin-3-yl | S |
| 293 | 2-$CH_3O$-Pyridin-3-yl | $N(CH_3)$ |
| 294 | 2-Cl-Pyridin-4-yl | NH |
| 295 | 4-Cl-Pyrimidin-2-yl | $OCH_2$ |
| 296 | 4-Cyano-Pyrimidin-2-yl | $CH_2O$ |
| 297 | 4-$CH_3$-Pyrimidin-2-yl | $CH_2CH_2O$ |
| 298 | 5-$CH_3$-Pyrimidin-2-yl | $CH_2CH_2CH_2O$ |
| 299 | 5-Cyano-pyrimidin-2-yl | S |
| 300 | 5-F-Pyrimidin-2-yl | $N(CH_3)$ |
| 301 | 2-Cl-Pyrimidin-4-yl | NH |
| 302 | 2-$CH_3$-Pyrimidin-4-yl | $OCH_2$ |
| 303 | 2-$CH_3S$-Pyrimidin-4-yl | $CH_2O$ |
| 304 | 6-Cl-Pyrazin-2-yl | $CH_2CH_2O$ |
| 305 | 6-Cl-Pyridazin-3-yl | $CH_2CH_2CH_2O$ |
| 306 | 6-Cl-Pyridazin-3-yl | S |
| 307 | 2-$CH_3$-Thiazol-4-yl | $N(CH_3)$ |
| 308 | 5-$CF_3$-1,3,4-Thiadiazol-2-yl | NH |
| 309 | 4-Cl-1,2,5-Thiadiazol-3-yl | $OCH_2$ |
| 310 | Pyrimidin-2-yl,N-oxide | $CH_2O$ |
| 311 | Pyrimidin-4-yl,1-N-oxide | $CH_2CH_2O$ |
| 312 | Pyrimidin-4-yl,3-N-oxide | $CH_2CH_2CH_2O$ |
| 313 | Pyridin-2-yl,N-oxide | S |
| 314 | Pyrazin-2-yl,1-N-oxide | $N(CH_3)$ |
| 315 | * | NH |
| 316 | 2-Cyano-$C_6H_4$ | $N(CH_3)$ |
| 317 | Pyridin-2-yl | SO |
| 318 | Pyridin-2-yl | $SO_2$ |
| 319 | 2-Cyano-$C_6H_4$ | $CH_2CH_2O$ |
| 320 | 2-$NO_2$—$C_6H_4$ | $CH_2CH_2O$ |
| 321 | 4-Cyano-$C_6H_4$ | $CH_2CH_2O$ |
| 322 | $C_6H_5$ | $CH_2CH_2CH_2O$ |
| 323 | 2-$NO_2$—$C_6H_4$ | $CH_2CH_2CH_2O$ |
| 324 | 2-HO—$C_6H_4$ | CONH |
| 325 | 2-$CF_3$—$C_6H_4$ | $CH_2CH_2O$ |
| 326 | 2-$CH_3$—$C_6H_4$ | $CH_2CH_2O$ |
| 327 | 2-$CH_3O$—$C_6H_4$ | $CH_2CH_2O$ |
| 328 | 2-F—$C_6H_4$ | $CH_2CH_2O$ |
| 329 | 2-HO—$C_6H_4$ | CSNH |
| 330 | 2-Cl—$C_6H_4$ | $CH_2CH_2O$ |
| 331 | $C_6H_5$ | CH(CN)O |
| 332 | 2,6-di-F—$C_6H_3$ | $CH_2CH_2O$ |
| 333 | $C_6H_5$ | $CH(CF_3)O$ |
| 334 | 2-Cl-6-F—$C_6H_3$ | $CH_2CH_2O$ |
| 335 | 2,6-di-Cl—$C_6H_3$ | $CH_2CH_2O$ |
| 336 | 2,6-di-F—$C_6H_3$ | $CH_2O$ |
| 337 | 2-$NO_2$—$C_6H_4$ | $CH_2O$ |
| 338 | $C_6H_5$ | (E)-CH = $CHCH_2O$ |
| 339 | 2-Cyano-$C_6H_4$ | NH |
| 340 | 2-HO—$C_6H_4$ | NH |
| 341 | 2-($CH_3O$)-$C_6H_4$ | NH |
| 342 | 2-Cyano-$C_6H_4$ | $SO_2O$ |
| 343 | 2,6-di-F—$C_6H_4$ | $OCH_2CH_2O$ |
| 344 | 2-Cl-6-$CF_3$—$C_6H_3$ | $CH_2O$ |
| 345 | 2-Cl—$C_6H_4$ | $CH_2CH_2CH_2O$ |
| 346 | 2-$CF_3$—$C_6H_4$ | $CH_2O$ |
| 347 | 2-F-6-Cl—$C_6H_3$ | $CH_2O$ |
| 348 | $C_6H_5$ | C≡$CCH_2O$ |
| 349 | $C_6F_5$ | $CH_2O$ |
| 350 | 2-Cyano-$C_6H_4$ | $CH_2O$ |
| 351 | 4-Cyano-$C_6H_4$ | $OCH_2CH_2O$ |
| 352 | $C_6H_5$ | $SCH_2CH_2O$ |
| 353 | 2-HO—$C_6H_4$ | N(CHO) |
| 354 | 2-Cyano-$C_6H_4$ | $SCH_2CH_2O$ |
| 355 | 2-Thienyl | $CH_2O$ |
| 356 | 2-Cyano-$C_6H_4$ | (E)-CH = $CHCH_2O$ |
| 357 | 2-Cyano-$C_6H_4$ | $OCH_2CH_2O$ |
| 358 | 2-Cyano-6-F-$C_6H_3$ | $OCH_2CH_2O$ |
| 359 | $C_6H_5$ | $CON(COC_6H_5)$ |
| 360 | 2-$CH_3$—$C_6H_4$ | S |
| 361 | 3-$CF_3$—$C_6H_4$ | (E)-CH = NO |
| 362 | Pyrrol-2-yl | (E)-C($CH_3$) = NO |

* For these values of Z and X see under "Chemical Formulae" later.

Table II comprises 362 compounds of the formula (I.4) with all the values of X and Z listed in Table I and with the value of A being hydrogen except where otherwise shown. That is, compounds numbers 1 to 362 of Table II are the same as those of Table I except that the 3- and 5-substituents of the 1,2,4-triazine ring in Table I are reversed in Table II and compound number 360A of Table II has an additional substituent in the triazine ring.

TABLE II

(Formula I.4)

| Compound No. | Z | X | A | Olefinic+ | Melting Point (° C.) |
|---|---|---|---|---|---|
| 360 | 2-$CH_3$—$C_6H_4$ | S | H | 7.47 | Gum |
| 360A | 2-$CH_3$—$C_6H_4$ | S | Cl | 7.49 | Gum |

Table III comprises 362 compounds of the formula (I.5) with all the values of X and Z listed in Table I. That is, compounds numbers 1 to 362 of Table III are the same as those of Table I except that the triazine ring is a 3,5-disubstituted 1,2,4-triazine in Table I and a 2, 4-disubstituted 1,3,5-triazine in Table III.

TABLE III (Formula I.5)

| Compound No. | Z | X | Olefinic+ | Melting Point (° C.) |
|---|---|---|---|---|
| 1 | $C_6H_5$ | S | 7.39 | 119–121 |
| 23 | $C_6H_5$ | $CH_2O$ | 7.45 | Gum |
| 31 | $C_6H_5$ | $CH_2S$ | 7.46 | Gum |
| 96 | $C_6H_5$ | $CH_2CH_2O$ | 7.46 | Gum |
| 133 | 4-F—$C_6H_4$ | $CH_2O$ | 7.46 | Gum |
| 322 | $C_6H_5$ | $CH_2CH_2CH_2O$ | 7.46 | Gum |
| 360 | 2-$CH_3$—$C_6H_4$ | S | 7.47 | 112–114 |
| 361 | 3-$CF_3$—$C_6H_4$ | (E)-CH =NO | 7.50 | 127–131 |
| 362 | Pyrrol-2-yl | (E)-C($CH_3$) =NO | 7.48 | Gum |

Table IV comprises 362 compounds of the formula (I.6) with all the values of X and Z listed in Table I. That is, compounds numbers 1 to 362 of Table IV are the same as those of Table I except that the triazine ring is an 0-linked 3,5-disubstituted 1,2,4-triazine in Table I and a S-linked 3,5-disubstituted 1,2,4-triazine in Table IV.

Table V comprises 362 compounds of the formula (I.7) with all the values of X and Z listed in Table I. That is, compounds numbers 1 to 362 of Table V are the same as those of Table I except that the triazine ring is an 0-linked 3,5-disubstituted 1,2,4-triazine in Table I and a S-linked 3,5-disubstituted 1,2,5-triazine in Table V.

Table VI comprises 362 compounds of the formula (I.8) with all the values of X and Z listed in Table I. That is, compounds numbers 1 to 362 of Table VI are the same as those of Table I except that the triazine ring is an 0-linked 3,5-disubstituted 1,2,4-triazine in Table I and a S-linked 2,4-disubstituted 1,3,5-triazine in Table VI.

TABLE VII

Selected Proton NMR Data

Table VII shows selected proton NMR data for compounds described in Table III. As already indicated, chemical shifts are measured in ppm from tetramethylsilane and deuterochloroform was used as solvent. The NMR instrument operated at a frequency of 270 MHz. The following abbreviations are used:

| Compound No (of Table III) | Proton NMR data |
|---|---|
| 1 | 3.53(3H,s); 3.65(3H,s); 6.98–7.07(1H,m); 7.16–7.36 (6H,m); 7.39(1H,s); 7.42–7.50(2H,m); 8.46(1H,s) ppm. |
| 23 | 3.58(3H,s); 3.66(3H,s); 5.37(2H,s); 7.17–7.43(9H,m); 7.45(1H,s); 8.61(1H,s) ppm. |
| 31 | 3.58(3H,s); 3.65(3H,s); 4.23(2H,s); 7.13–7.27(5H,m); 7.28–7.45(3H,m); 7.46(1H,s); 8.56(1H,s) ppm. |
| 96 | 3.04(2H,t); 3.58(3H,s); 3.70(3H,s); 4.52(2H,t); 7.46(1H,s); 8.60(1H,s) ppm. |
| 133 | 3.57(3H,s); 3.68(3H,s); 5.31(2H,s); 6.95(2H,t); 7.2–7.5(6H,m); 7.46(1H,s); 8.61(1H,s) ppm. |
| 322 | 2.09(2H,m); 2.75(2H,t); 3.60(3H,s); 3.72(3H,s); 4.36(2H,t); 7.46(1H,s); 8.60(1H,s); ppm. |
| 362 | 2.40(3H,s); 3.61(3H,s); 3.74(3H,s); 6.25–6.29(1H,m); 6.66(1H,br s); 6.95(1H,br s); 7.20–7.45(4H,m); 7.48(1H,s); 8.70(1H,s); 9.77(1H,br s) ppm. | br = broad
s = singlet
d = doublet
t = triplet
q = quartet

| Compound No (of Table III) | Proton NMR data |
|---|---| m = multiplet
ppm = parts per million

The compounds of the invention of formula (I) [equivalent to (IA) when W is the group $CH_3O_2C.C$=$CH.OCH_3$ and $Z^1$ is Z; and equivalent to (IB) when W is the group $CH_3O_2C.C$=$CH.OCH_3$] can be prepared by the steps shown in Schemes I and II. In these Schemes, K, L, M, Z, T and X, are as defined above; $Z^1$ is Z or a group which can be converted by standard procedures described in the chemical literature into Z; W is $CH_3O_2C.C$=$CH.OCH_3$ or a group that can be transformed into $CH_3O_2C.C$=$CH.OCH_3$ using methods previously described such as in EP-A-0242081; U is a leaving group such as a halogen or $CH_3SO_2$—; V is hydrogen or a metal (such as sodium); and Y is a group which can be converted by standard procedures described in the chemical literature into the group ZX. The reactions shown in Schemes I and II are performed either in a suitable solvent or without a solvent, and at a suitable temperature.

Thus compounds of formula (IA) (equivalent to compounds of the invention when W is $CH_3O_2C.C$=$CH.OCH_3$ and $Z^1$ is Z) can be prepared by treatment of triazines of formula (IV) with phenols/thiophenols or phenolates/thiophenolates of formula (II) or by treatment of triazines of formula (V) with substituted benzenes of formula (III) (Scheme I). In each case, the reaction is carried out in the presence of a base (such as potassium carbonate) if V is hydrogen.

Compounds of formula (IB) (equivalent to the compounds of the invention when W is $CH_3O_2C.C$=$CH.OCH_3$) can be prepared from triazines of formula (VI) (Scheme II). The term Y in formulae (VI), (VII) and (VIII) represents a group which can be converted by standard procedures described in the chemical literature into the group ZX—; for example, Y may be a halogen (such as fluorine, chlorine or bromine) or —OH, —SH, —$NHR^4$, —$CO_2H$, —COCl, —$CHR^1OH$, —$C(O)R^1$, —$CHR^1$—U (where U is a leaving group such as a halogen), —$SO_2OH$, —$SO_2Cl$, —$CHR^1P(O)(OR)_2$ or —$CHR^1P^+R_3$ (counter-ion)$^-$. Compounds of formula (VI) in which W is $CH_3O_2C.C$=$CH.OCH_3$ and Y has the values listed in the preceding sentence are especially valuable intermediates for the preparation of the compounds of the invention.

Triazines of formula (VI) can be prepared by treatment of phenols/thiophenols or phenolates/thiophenolates of formula (II) with triazines of formula (VII) or by treatment of substituted benzenes of formula (III) with triazines of formula (VIII) (Scheme II). In each case, the reaction is carried out in the presence of a base (such as potassium carbonate) if V is hydrogen.

Modifications to the group W may be made at any appropriate stage in the pathways shown in Schemes I and II. For example, if W is the group —$CH_2CO_2CH_3$ during the conversion of (VI) into (IB) (Scheme II), it may be converted at the last stages of the synthesis into the group $CH_3O_2C.C$=$CH.OCH_3$.

The substitutent A (one of K, L, M having the value CA wherein A is as defined above) as well as any substituents on the carbocyclic or heterocyclic ring Z may also be modified at any appropriate reaction step. If, for example, Y is a halogen such as chlorine, it may be removed at an appropriate stage of the synthesis (such as the last stage) to give the corresponding triazine in which A is hydrogen.

Modifications to the linking group X (such as reducing an olefinic bond or oxidising a sulphur atom) may also be made at any appropriate reaction step.

Triazines of formulae (IV), (V), (VII) and (VIII) can be prepared by standard methods described in the literature. Compounds of formulae (II) and (III) can also be made by standard methods or, when W is $CH_3O_2C.C=CH.OCH_3$, can be made by methods described in EP-A-0242081 (T is oxygen) and EP-A-0178826 respectively.

In a further aspect the invention provides processes as herein-described for preparing the compounds of formula (I). It also provides an intermediate chemical of formula (VI).

The compounds are active fungicides and may be used to control one or more of the following pathogens: *Pyricularia oryzae* on rice; *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants; *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; *Helminthosporium* spp., Rhynchosporium spp., Septoria spp., Pyrenophora spp., *Pseudocercosporella herpotrichoides* and *Gaeumannomyces graminis* on cereals; *Cercospora arachidicola* and *Cercosporidium personata* on peanuts and other Cercospora species on other hosts, for example, sugar beet, bananas, soya beans and rice; *Botrytis cinerea* (grey mould) on tomatoes, strawberries, vegetables, vines and other hosts; Alternaria spp. on vegetables (e.g. cucumber), oil-seed rape, apples, tomatoes and other hosts; *Venturia inaegualis* (scab) on apples; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against pathogens including Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that these compositions comprise 0.0001 to 95%, more preferably 0.001 to 60%, even more preferably 0.01 to 1%, of the compound.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrol-idone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and tri-isopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (±)-cis-1-(4-chlorophenyl)-2-(1H-1,2,4--triazol-1-yl) cycloheptanol, (2RS,3RS)-1-[3-(2-chlorophenyl)-2-(4-fluoro-phenyl)oxiran-2-ylmethyl]-1H-1,2,4-triazole, (RS)-1-aminopropylphosphonic acid, (RS)-4-(4-chlorophenyl)-2-phenyl-2-(1H-1,2,4-triazol-1-ylmethyl)butyronitrile, (Z)-N-but-2-enyloxymethyl-2-chloro-2', 6'-diethylacetanilide, 1-(2-cyano-2-methoxyiminoacetyl)-3-ethyl urea, 3-(2,4-dichlorophenyl)-2--(1H-1,2,4-triazol-1-yl)quinazolin-4 (3H)-one, 4-(2,2-difluoro-1,3-benzodi-oxol-4-yl)pyrrole-3-carbonitrile, 4-bromo-2-cyano-N,N-dimethyl-6-trifluoro-methylbenzimidazole-1-sulphonamide, 5-ethyl-5,8-dihydro-8-oxo(1,3)-dioxol-(4,5-g) quinoline-7-carboxylic acid, α-[N-(3-chloro-2,6-xylyl)-2-methoxy-acetamido]-γ-butyrolactone, aldimorph, anilazine, benalaxyl, benomyl, biloxazol, binapacryl, bitertanol, blasticidin S, bromuconazole, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methyl-thioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, poxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, tebuconazole, techlofthalam, tecnazene, tetraconazole, thiabendazole, thicyofen, thiophanate-methyl, thiram, tolclofos-methyl, triacetate salt of 1,1'-iminodi (octamethylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di-methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. Throughout the Examples, the term 'ether' refers to diethyl ether, magnesium sulphate was used to dry solutions, and solutions were concentrated under reduced pressure. Reactions involving water-sensitive intermediates were performed under an atmosphere of nitrogen and solvents were dried before use, where appropriate. Unless otherwise stated, chromatography was performed on a column of silica gel as the stationary phase. Where shown, infrared and NMR data are selective; no attempt is made to list every absorption in all cases. $^1H$ NMR spectra were recorded using $CDCl_3$ solutions unless otherwise stated. (E)-Methyl 2-(2-hydroxyphenyl)-3-methoxypropenoate, used as an intermediate in two of the following Examples, was prepared as described in Example 3 of EP-A-0242081. The following abbreviations are used throughout.

| | |
|---|---|
| DMF = N,N-dimethylformamide | s = singlet |
| NMR = nuclear magnetic resonance | m = multiplet |
| IR = infrared | ppm = parts per million |
| m.p. = melting point | |

EXAMPLE 1

This Example illustrates the preparation of (E)-methyl 2-[2-(4-phenylthio-1,3,5-triazin-2-yloxy)-phenyl]-3-methoxypropenoate (Compound No. 1 of Table III).

To a stirred solution of 2,6-dichloro-1,3,5-triazine (0.3 g, 2 mmol; made according to R L N Harris, Synthesis, 1981, 907) and potassium carbonate (0.28g, 2 mmol) in dry acetonitrile (25 ml) at 0° C. under an atmosphere of nitrogen was added dropwise a solution of (E)-methyl 2-(2-hydroxyphenyl)-3-methoxypropenoate (0.42 g, 2 mmol) in dry acetonitrile (7 ml). Anhydrous caesium fluoride (0.30 g, 2 mmol) and a catalytic amount of 18-crown-6 were added with stirring and the temperature was allowed to rise to room temperature. After stirring overnight, the reaction mixture was filtered and evaporated to leave a yellow/orange paste. Chromatography (eluent diethyl ether) afforded (E)-methyl 2-[2-(4-chloro-1,3,5-triazin-2-yloxy)phenyl]-3-methoxypropenoate (0.42 g) as a white solid, m.p. 137–140° C.; IR max. 1704, 1631 $cm^{-1}$; $^1H$ NMR ($CDCl_3$) δ3.63(3H, s); 3.75(3H,s); 7.19–7.29(1H,m); 7.31–7.45(3H,m); 7.47 (1H,s); 8.74(1H,s) ppm.

Thiophenol (0.207 g, 1.88 mmol) and potassium carbonate (0.26 g, 1.88 mmol) were stirred together in DMF (35 ml) at 60° C. After 15 minutes, a solution of (E)-methyl 2-[2-(4-chloro-1,3,5-triazin-2-yloxy)phenyl]-3-methoxypropenoate (0.55g, 1.71 mmol) in DMF (10 ml) was added and the mixture stirred at 60° C. for a further 2 hours. The reaction mixture was poured into water and then extracted with ether (x3). The combined organic layers were washed with dilute sodium hydroxide solution (x2) and water (x3), dried, filtered and evaporated to give a yellow gum (317 mg). Chromatography (eluent ether) afforded the title compound as a yellow solid (161 mg, 25%); m.p. 119–121° C.; IR maxima 1712, 1632 $cm^{-1}$; $^1H$ NMR as in Table VII.

EXAMPLE 2

This Example illustrates the preparation of (E)-methyl 2-[2-(4-phenethyloxy-1,3,5-triazin-2-yloxy) -phenyl]-3-methoxypropenoate (Compound No. 96 of Table III).

Phenethyl alcohol (126 mg, 1.03 mmol) in dry DMF (5 ml) was added to a suspension of sodium hydride (45 mg, 1.03 mmol, 55% dispersion in oil) in dry DMF (5 ml). After stirring at room temperature under nitrogen for 15 minutes, a solution of (E)-methyl 2-[2-(4-chloro-1,3,5-triazin-2-yloxy)-phenyl]-3-methoxypropenoate (300 mg, 0.933 mmol, prepared as described in Example 1) in DMF (10 ml) was added dropwise and the resulting mixture was stirred overnight. The reaction mixture was diluted with water and then extracted with ether. The organic layers were washed with water, dried, filtered and evaporated. Chromatography of the residue (eluent ether) afforded the title compound (31 mg) as a yellow gum; $^1H$ NMR as in Table VII; mass spectrum m/e 407 ($M^+$).

EXAMPLE 3

This Example illustrates the preparation (E)-methyl 2-[2-(6-chloro-3-[2-methylphenylthio]-1,2,4-triazin-5-yloxy) phenyl]-3-methoxypropenoate and (E)-methyl 3-methoxy-2-[2-(3-[2-methylphenylthio]-1,2,4-triazin-5-yloxy)-phenyl]propenoate (Compounds Nos. 360A and 360 respectively of Table II).

3,5,6-Trichloro-1,2,4-triazine (0.50 g) was dissolved in dry tetrahydrofuran (8 ml) and dry potassium carbonate (0.37 g) and 4Å molecular sieves (180 mg, activated overnight at 180° C.) were added. The stirred mixture was cooled to 0° C. and a solution of o-thiocresol (0.36 g) in dry tetrahydrofuran (4 ml) was added dropwise. After 45 minutes at 0–5° C. and standing overnight at 10° C., the mixture was diluted with dichloromethane (20 ml) and filtered through Hyflo Supercel filter aid covered with a layer of Merck silica 60. The filtrate was concentrated under reduced pressure to afford a single dichloro-(2-methylphenylthio)-1, 2,4-triazine (unidentified regioisomer) as a yellow oil (0.86 g) which crystallised on standing. Recrystallisation from ether-n-hexane yielded a pale yellow powder (0.57 g, 77%); m.p. 93–95° C.; IR max (nujol mull): 1460, 1250 $cm^{-1}$; $^1H$ NMR: δ2.38 (3H,s), 7.24–7.37(1H,m), 7.37–7.54(3H,m) ppm.

To a stirred solution of the dichloro-(2-methylphenylthio)-1,2,4-triazine formed in the reaction above (0.35 g) in dry acetonitrile (10 ml) was added dry potassium carbonate (0.18 g), followed by a solution of (E)-methyl 2-(2-hydroxyphenyl)-3-methoxypropenoate (0.27 g) in dry acetonitrile (2 ml), in one portion, at room temperature. A catalytic amount of 18-crown-6 and dry caesium fluoride (0.20 g) were then added. After stirring at room temperature for 11.5 hours, the mixture was diluted with acetonitrile (25 ml) and filtered through Hyflo Supercel filter aid. The filtrate was concentrated under reduced pressure and the residue was chromatographed twice using first ether-n-hexane (1:1) and then n-hexane-dichloromethane-acetonitrile (16:4:1) as eluent to afford (E)-methyl 2-[2-(6-chloro-3-[2-methylphenylthio]-1,2,4-triazin-5-yloxy)-phenyl]-3-methoxypropenoate as a pale yellow gum (0.16 g, 28%); IR max (nujol mull): 1710, 1630 cm$^{-1}$; $^1$H NMR δ2.27(3H,s), 3.64(3H,s), 3.75(3H,s), 6.90–6.97(1H,m), 7.09–7.39(6H,m), 7.45–7.53(1H,m), 7.49(1H,s) ppm.

Potassium carbonate (0.115 g), 5% palladium on carbon (0.025 g) and water (0.5 ml) were added to a solution of (E)-methyl 2-[2-(6-chloro-3-[2-methylphenylthio]-1,2,4-triazin-5-yloxy)phenyl]-3-methoxypropenoate (0.106 g) in tetrahydrofuran (12 ml). Hydrogen gas was passed through the stirred mixture for 10.25 hours and then more dry potassium carbonate (0.100 g) and 10% palladium on carbon (0.030 g) were added. After hydrogen had been passed for a total of 21.25 hours, the mixture was diluted with dichloromethane (15 ml) and water (10 ml) and filtered through Hyflo Supercel filter aid. The dichloromethane solution was separated from the filtrate and the aqueous layer was extracted with further dichloromethane (2×15 ml). The combined dichloromethane solution and extracts were dried and concentrated under reduced pressure. Chromatography of the residue using ether-n-hexane (5:2) as eluent afforded (E)-methyl 3-methoxy-2-[2-(3-[2-methylphenylthio]-1,2,4-triazin-5-yloxy]phenyl]propenoate as a pale yellow gum (23 mg) containing 21% of an unidentified impurity. IR max (dichloromethane solution): 1710, 1630cm$^{-1}$; $^1$H NMR δ2.31(3H,s), 3.58(3H,s), 3.70(3H,s), 6.88–7.00(1H,m), 7.11–7.37(6H,m), 7.47(1H,s), 7.49–7.57(1H,m), 8.59(1H,s) ppm.

The following are examples of compositions suitable for agricultural and horticultural purposes which can be formulated from the compounds of the invention. Such compositions form another aspect of the invention. Percentages are by weight.

EXAMPLE 4

An emulsifiable concentrate is made up by mixing and stirring the ingredients until all are dissolved.

| Compound No.1 of Table III | 10% |
|---|---|
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 5

The active ingredient is dissolved in methylene dichloride and the resultant liquid sprayed on to the granules of attapulgite clay. The solvent is then allowed to evaporate to produce a granular composition.

| Compound No.1 of Table III | 5% |
|---|---|
| Attapulgite granules | 95% |

EXAMPLE 6

A composition suitable for use as a seed dressing is prepared by grinding and mixing the three ingredients.

| Compound No.1 of Table III | 50% |
|---|---|
| Mineral oil | 2% |
| China clay | 48% |

EXAMPLE 7

A dustable powder is prepared by grinding and mixing the active ingredient with talc.

| Compound No.1 of Table III | 5% |
|---|---|
| Talc | 95% |

EXAMPLE 8

A suspension concentrate is prepared by ball milling the ingredients to form an aqueous suspension of the ground mixture with water.

| Compound No.1 of Table III | 40% |
|---|---|
| Sodium lignosulphonate | 10% |
| Bentonite clay | 1% |
| Water | 49% |

This formulation can be used as a spray by diluting into water or applied directly to seed.

EXAMPLE 9

A wettable powder formulation is made by mixing together and grinding the ingredients until all are thoroughly mixed.

| Compound No.1 of Table III | 25% |
|---|---|
| Sodium lauryl sulphate | 2% |
| Sodium lignosulphonate | 5% |
| Silica | 25% |
| China clay | 43% |

EXAMPLE 10

The compounds were tested against a variety of foliar fungal diseases of plants. The technique employed was as follows.

The plants were grown in John Innes Potting Compost (No.1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formultions (100 ppm active ingredient except where otherwise indicated) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were incoulated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

disease control was recorded by the following grading:

4=no disease
3=trace-5% of disease on untreated plants
2=6-25% of disease on untreated plants
1=26-59% of disease on untreated plants
0=6-100% of disease on untreated plants The results are shown in Table VIII.

TABLE VIII

| Compound No | Table No | Pr | Egt | Sn | Po | Tc | Vi | Pv | Pil |
|---|---|---|---|---|---|---|---|---|---|
| 1 | III | 4 | 4 | 4 | 3 | — | — | 4 | — |
| 23 | III | 3[a] | 0[a] | 0[a] | 0[a] | — | 4[a] | 4[a] | 2[a] |
| 31 | III | — | 4 | — | 4 | 2 | 4 | 4 | 4 |
| 96 | III | 4[a] | 0[a] | 3[a] | — | — | 4[a] | 4[a] | 2[a] |
| 133 | III | 4[a] | 0[a] | 0[a] | — | — | 4[a] | 4[a] | 4[a] |
| 322 | III | 4[a] | 0[a] | 3[a] | — | — | 4[a] | 4[a] | 3[a] |
| 360 | III | — | 4 | — | 4 | 4 | 4 | 4 | 4 |
| 361 | III | 0 | 1 | 0 | 1 | 0 | 0 | 4 | 0 |
| 362 | III | 0[a] | 0[a] | 0[a] | 0[a] | 0[a] | 1[a] | 0[a] | 0[a] |

—No result
[a]10 ppm foliar application only.
Key to Diseases
Pr *Puccinia recondita*
Egt *Erysiphe graminis tritici*
Sn *Septoria nodorum*
Po *Pyricularia oryzae*
Tc *Thanatephorus cumcumeris*
Vi *Venturia inaequalis*
Pv *Plasmopara viticola*
Pil *Phytophthora infestans lycopersici*

CHEMICAL FORMULAE
(in description)

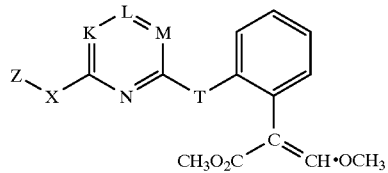
(I)

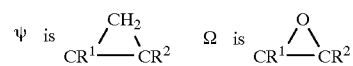

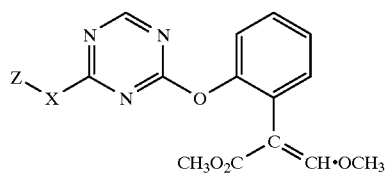
(I.1)

-continued

CHEMICAL FORMULAE
(in description)

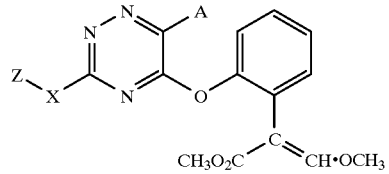
(I.2)

TABLE I

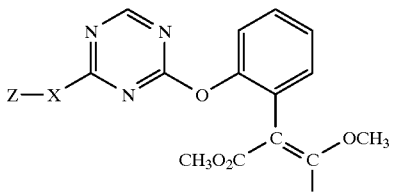
(I.3)

TABLE II

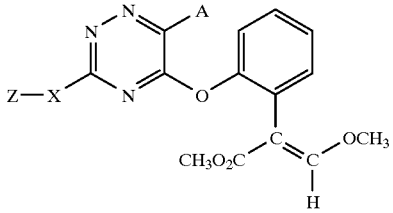
(I.4)

TABLE III

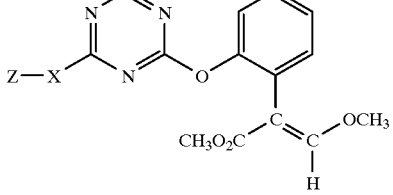
(I.5)

TABLE IV

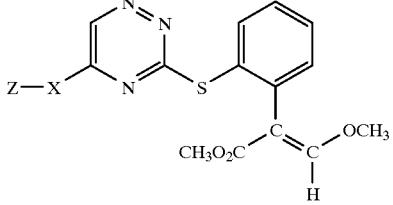
(I.6)

TABLE V

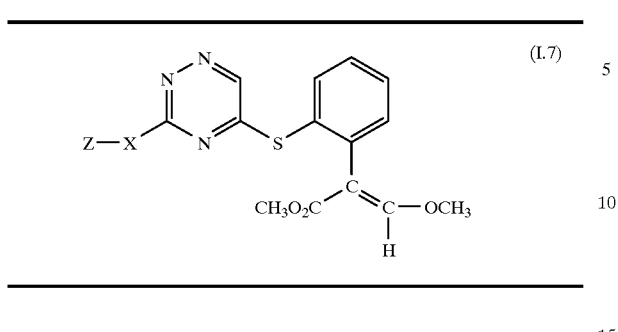
(I.7)

TABLE VI

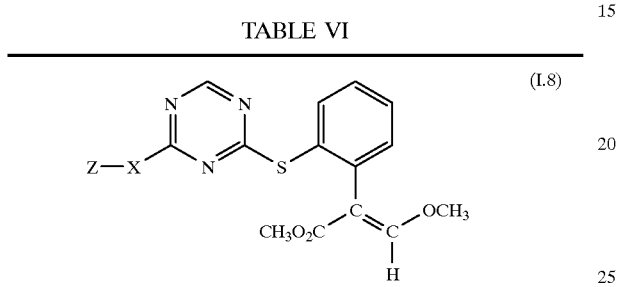
(I.8)

\* X for Compound No 117 is

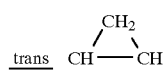
trans

\* X for Compound No 118 is

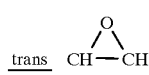
trans

\* Z for Compound No 315 is

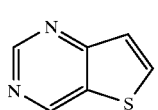

Scheme I

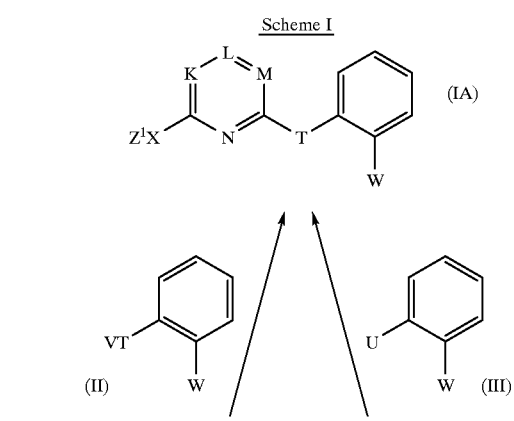

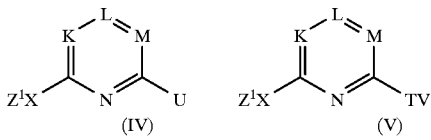

Scheme II

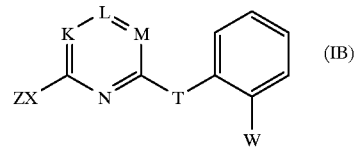

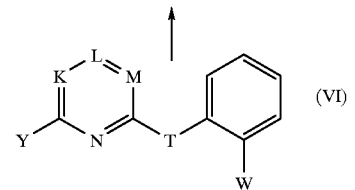

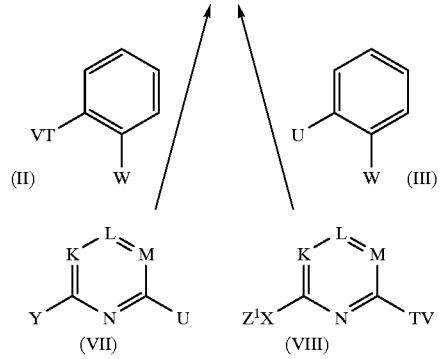

We claim:
1. A compound having the formula (I):

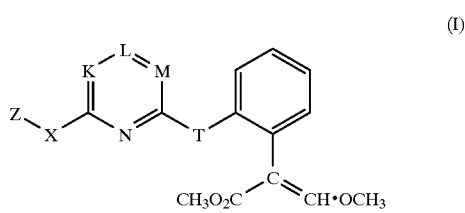

in which any two of K, L and M are nitrogen and the other is CA wherein A is H, halogen, $C_{1-4}$ alkyl, $C_{1-4}$ alkoxy, cyano, nitro or trifluoromethyl;

X is selected from the group consisting of $S(O)_n$, $NR^4$ $N(CHO)$, $CR^1R^2CHR^6$, $CO$, $CR^1(OR^2)$, $C=CR^1R^2$, $CHR^1CHR^2$, $CR^1=CR^2$, $CHR^1CR^2=CH$, $C\equiv C$, $OCHR^1$, $CHR^1O$, $CH(CF_3)O$, $CH(CN)O$, $OCHRO^1O$, $S(O)_nCHR^1$, $S(O)_nCHR^1O$, $CHR^1S(O)_n$, $CHR^1OSO_2NR^4CHR^1$, $CHR^1NR^4$, $CO_2$, $O_2C$, $SO_2O$, $OSO_2$, $CO.CO$, $COCHR^1$, $COCHR^1O$, $CHR^1CO$, $CHOH.CHR^1$, $CHR^1.CHOH$,

CONR$^4$, OCONR$^4$, NR$^4$CO, CSNR$^4$, OCS.NR$^4$, SCO.NR$^4$, NR$^4$CO$_2$, NR$^4$CS, NR$^4$CSO, NR$^4$COS, NR$^4$CONR$^4$, S(O)$_n$NR$^4$, NR$^4$S(O)$_n$, CS$_2$, S$_2$C, CO.S., SCO, N=N, N=CR$^1$, CR$^1$=N, CHR$^1$CHR$^2$CH(OH), CHR$^1$OCO, CHR$^1$SCO, CHR$^1$NR$^4$CO, CHR$^1$NR$^4$CONR$^4$, CHR$^1$CHR$^2$CO, O.N=CR$^1$, CHR$^1$O.N=CR$^2$, CO.OCR$^1$R$^2$, CHR$^1$CHR$^2$CHR$^3$, OCHR$^1$CHR$^2$, (CH$_2$)$_m$O, CHR$^1$OCHR$^2$, CHR$^1$CHR$^2$O, OCHR$^1$CHR$^2$O, S(O)$_n$CHR$^1$CHR$^2$, SCHR$^1$CHR$^2$O, CHR$^1$S(O)$_n$CHR$^2$, CHR$^1$CHR$^2$S(O)$_n$, CR$^1$=NNR$^4$, CR$^1$=NO, NR$^4$N=CR$^1$, CHR$^1$CONR$^2$, CHR$^1$OCO.NR$^2$, CH=CHCH$_2$O, C≡CCH$_2$O, COCHR$^1$CHR$^2$O, and (R$^5$)$_2$P$^+$CHR$^2$Q$^-$; where R$^1$, R$^2$ and R$^3$, which may be the same or different, are H, C$_{1-4}$ alkyl or phenyl; R$^4$ is H, C$_{1-4}$ alkyl or COR$^1$; R$^5$ is optionally substituted phenyl; R$^6$ is substituted phenyl; Q$^-$ is a halide anion; n is 0, 1 or 2; and m is 3, 4 or 5;

T is oxygen or sulphur; and

Z is a carbocyclic ring optionally substituted with one or more of the following: halo, hydroxy, oxo, mercapto, C$_{1-4}$ alkyl, C$_{2-4}$ alkenyl, C$_{2-4}$ alkynyl, C$_{1-4}$ alkoxy, C$_{2-4}$ alkenyloxy, C$_{2-4}$ alkynyloxy, halo(C$_{1-4}$)alkyl, halo(C$_{1-4}$)alkoxy, C$_{1-4}$ alkylthio, hydroxy(C$_{1-4}$)alkyl, C$_{1-4}$alkoxy(C$_{1-4}$)alkyl, C$_{3-6}$ cycloalkyl, C$_{3-6}$ cycloalkyl(C$_{1-4}$)alkyl, optionally substituted aryl, optionally substituted aryloxy, optionally substituted aryl(C$_{1-4}$)alkyl, in which the alkyl moiety is optionally substituted with hydroxy, optionally substituted aryl(C$_{2-4}$)alkenyl, optionally substituted aryl(C$_{1-4}$)alkoxy, optionally substituted aryloxy(C$_{1-4}$)alkyl, acyloxy, cyano, thiocyanato, nitro, —NR'R", —NHCOR', —NHCONR'R", —CON'R", —COOR', —OSO$_2$R', —COR', —CR'=NR" or —N=CR'R" in which R' and R" are independently hydrogen, C$_{1-4}$ alkyl, C$_{1-4}$ alkoxy, C$_{1-4}$ alkylthio, C$_{3-6}$ cycloalkyl, C$_{3-6}$cycloalkyl(C$_{1-4}$) alkyl, phenyl or benzyl, the phenyl and benzyl groups being optionally substituted with halogen, C$_{1-4}$ alkyl or C$_{1-4}$ alkoxy, or any two substituents of the carbocyclic ring Z when adjacent to one another, may together with the carbon atoms to which they are attached join to form a 5- or 6-membered ring; substituents which may be present in the aryl rings of any of the foregoing substituents and in the phenyl rings of R$^5$ and R$^6$ being one or more of the following: halo, hydroxy, mercapto, C$_{1-4}$ alkyl, C$_{2-4}$ alkenyl, C$_{2-4}$ alkenyloxy, C$_{2-4}$ alkynyloxy, halo(C$_{1-4}$)alkyl, halo(C$_{1-4}$)alkoxy, C$_{1-4}$ alkylthio, hydroxy(C$_{1-4}$)-alkyl, C$_{1-4}$alkoxy(C$_{1-4}$)alkyl, C$_{3-6}$ cycloalkyl, C$_{3-6}$ cycloalkyl-(C$_{1-4}$)alkyl, alkanoyloxy, benzoyloxy, cyano, thiocyanato, nitro, —NR'R", —NHCOR', —NHCONR'R", —CON'R", —COOR', —OSO$_2$R', —COR', —CR'=NR" or —N=CR'R" in which R' and R" have the meanings given above.

2. A compound according to claim 1 in which K and M are both nitrogen; L is CH; and Z is optionally substituted phenyl.

3. A compound according to claim 1 in which Z is selected from the group consisting of phenyl, naphthyl, cyclopentyl, cyclohexyl or cyclohexenyl, any of which is optionally substituted.

4. A compound having the formula (I.1)

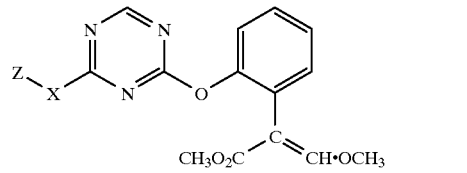

(I.1)

in which Z is phenyl optionally substituted with halo, C$_{1-4}$ alkyl or trifluoromethyl; and X is S, CH$_2$O, CH$_2$S, CH$_2$CH$_2$O, CH$_2$CH$_2$CH$_2$O or (E)—CH=NO.

5. A compound having the formula (I.2):

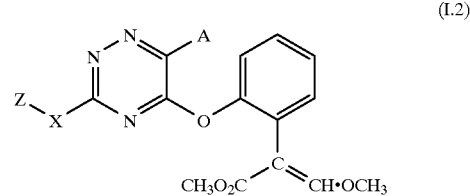

(I.2)

in which Z is phenyl optionally substituted with C$_{1-4}$ alkyl; X is S; and A is H or Cl.

6. A fungicidal composition comprising a fungicidally effective amount of a compound according to claim 1 and a fungicidally acceptable carrier or diluent therefor.

7. A method of combating fungi which comprises applying to plants, to the seeds of plants or to the locus of the plants or seeds, a compound according to claim 1 or a composition according to claim 4.

8. A compound in accordance with claim 1 wherein X is selected from the group consisting of NR$^4$, N(CHO), CR$^1$R$^2$, CHR$^6$, CO, CR$^1$(OR$^2$), C=CR$^1$R$^2$, CHR$^1$CHR$^2$, CR$^1$=CR$^2$, CHR$^1$CR$^2$=CH, C=C, OCHR$^7$, CHR$^1$O, CH(CF$_3$)O, CH(CN)O, OCHR$^1$O, S(O)$_n$CHR$^1$, S(O)$_n$CHR$^1$O, CHR$^1$S(O)$_n$, CHR$^1$OSO$_2$NR$^4$CHR$^1$, CHR$^1$NR$^4$, CO$_2$, O$_2$C, SO$_2$O, OSO$_2$, CO.CO, COCHR$^1$, COCHR$^1$O, CHR$^1$CO, CHOH.CHR$^1$, CHR$^1$.CHOH,

CONR$^4$, OCONR$^4$, NR$^4$CO, CSNR$^4$, OCS.NR$^4$ SCO.NR$^4$, NR$^4$CO$_2$, NR$^4$CS, NR$^4$CSO, NR$^4$COS, NR$^4$CONR$^4$, S(O)$_n$NR$^4$, NR$^4$S(O)$_n$, CS$_2$, S$_2$C, CO.S., SCO, N=N, N=CR$^1$, CR$^1$=N, CHR$^1$CHR$^2$CH(OH), CHR$^1$OCO, CHR$^1$SCO, CHR$^1$NR$^4$CO, CHR$^1$NR$^4$CONR$^4$, CHR$^1$CHR$^2$CO, O.N=CR$^1$, CHR$^1$O.N=CR$^2$, CO.OCR$^1$R$^2$, CHR$^1$CHR$^2$CHR$^3$, OCHR$^1$CHR$^2$, (CH$_2$)$_m$O, CHR$^1$OCHR$^2$, CHR$^1$CHR$^2$O, OCHR$^1$CHR$^2$O, S(O)$_n$CHR$^1$CHR$^2$, SCHR$^1$CHR$^2$O, CHR$^1$S(O)$_n$CHR$^2$, CHR$^1$CHR$^2$S(O)$_n$, CR$^1$=NNR$^4$, CR=NO, NR$^4$N=CR$^1$, CHR$^1$CONR$^2$, CHR$^1$OCO.NR$^2$, CH=CHCH$_2$O, C=CCH$_2$O, COCHR$^1$CHR$^2$O, and (R$^5$)$_2$P$^+$CHR$^2$Q$^-$; where R$^1$, R$^2$ and R$^3$, which may be the same or different, are H, C$_{1-4}$ alkyl or phenyl; R$^4$ is H, C$_{1-4}$ alkyl or COR$^1$; R$^5$ is optionally substituted phenyl; R$^6$ is substituted phenyl; R$^7$ is C$_1$–C$_4$ alkyl or phenyl; Q$^-$ is a halide anion; n is 0, 1 or 2; and m is 3, 4 or 5.

* * * * *